(12) United States Patent
Klepp et al.

(10) Patent No.: US 7,118,875 B2
(45) Date of Patent: Oct. 10, 2006

(54) ANALYTE DETERMINATION USING A GENERAL PURPOSE STRUCTURE OF AN ANALYTICAL ELEMENT

(75) Inventors: Jürgen Klepp, Karlsruhe (DE); Gerhard Hiller, Mannheim (DE); Alfons Nichtl, Hohenpeissenberg (DE); Thomas Fischer, Rauenberg (DE); Martina Hösch, Mannheim (DE)

(73) Assignee: Roche Diagnostics GmbH, (DE)

( * ) Notice: Subject to any disclaimer, the term of this patent is extended or adjusted under 35 U.S.C. 154(b) by 183 days.

(21) Appl. No.: 10/748,560

(22) Filed: Dec. 30, 2003

(65) Prior Publication Data

US 2004/0152142 A1 Aug. 5, 2004

Related U.S. Application Data

(63) Continuation of application No. 09/215,979, filed on Dec. 18, 1998, now Pat. No. 6,703,196.

(30) Foreign Application Priority Data

Dec. 24, 1997 (DE) ................. 197 57 980
Apr. 15, 1998 (DE) ................. 198 16 550

(51) Int. Cl.
*G01N 33/53* (2006.01)
*G01N 33/566* (2006.01)

(52) U.S. Cl. ................. 435/7.1; 435/4; 435/7.9; 436/501; 436/518; 422/56; 422/61

(58) Field of Classification Search ................. 435/4, 435/7.1, 7.9; 436/501, 518; 422/56, 61
See application file for complete search history.

(56) References Cited

U.S. PATENT DOCUMENTS

| | | | |
|---|---|---|---|
| 4,281,061 A | 7/1981 | Zuk et al. | |
| 4,477,575 A | 10/1984 | Vogel et al. | |
| 4,515,889 A | 5/1985 | Klose et al. | |
| 4,791,056 A * | 12/1988 | Sizto et al. | ................. 435/7.91 |
| 4,806,311 A * | 2/1989 | Greenquist | ................. 422/56 |
| 4,861,711 A | 8/1989 | Friesen et al. | |
| 5,118,609 A | 6/1992 | Baier et al. | |
| 5,141,850 A | 8/1992 | Cole et al. | |
| 5,354,692 A * | 10/1994 | Yang et al. | ................. 436/514 |
| 5,478,752 A | 12/1995 | Lerch et al. | |
| 5,591,645 A | 1/1997 | Rosenstein | |
| 5,719,034 A | 2/1998 | Kiser et al. | |
| 5,795,783 A * | 8/1998 | Kyle et al. | ................. 436/8 |

FOREIGN PATENT DOCUMENTS

| | | | |
|---|---|---|---|
| EP | 0 291 194 A1 | | 4/1988 |
| EP | 0 328 106 | * | 8/1989 |
| EP | 0 630 974 | * | 12/1994 |
| WO | WO 92/20702 | | 11/1992 |
| WO | WO 96/03423 | | 2/1996 |
| WO | WO 97/06439 | * | 2/1997 |
| WO | WO 97/34147 | | 9/1997 |

OTHER PUBLICATIONS

Frens, G., *Controlled Nucleation for the Regulation of the Particle Size in Monodisperse Gold Suspension*, Nature Physical Science, 1973, vol. 241, pp. 20-22.

Roth, J., *The Colloidal Gold Marker System for Light and Electron Microscopic Cytochemistry*, in G.R. Bullock, et al, Techniques in Immunocytochemistry, vol. 2, pp. 217-284, Academic Press, New York (1983).

* cited by examiner

*Primary Examiner*—Long V. Le
*Assistant Examiner*—Lisa V Cook
(74) *Attorney, Agent, or Firm*—McDonnell Boehnen Hulbert & Berghoff LLP

(57) ABSTRACT

The invention concerns an analytical element for the determination of an analyte containing in or on material which enables liquid transport between zones, a sample application zone and a detection zone located downstream thereof, wherein the detection zone contains a partner 1 of a specific binding pair 1 immobilized in such a manner that it is able to bind to partner 2 of the specific binding pair 1 which is not the analyte when it contacts it, wherein a labelled partner 1 of a specific binding pair 2 is present upstream of the detection zone impregnated on a material such that it can be detached by liquid and is able to bind to partner 2 of the specific binding pair 2 which is not the analyte when this contacts it as well as a method for the determination of an analyte using this analytical element.

22 Claims, 1 Drawing Sheet

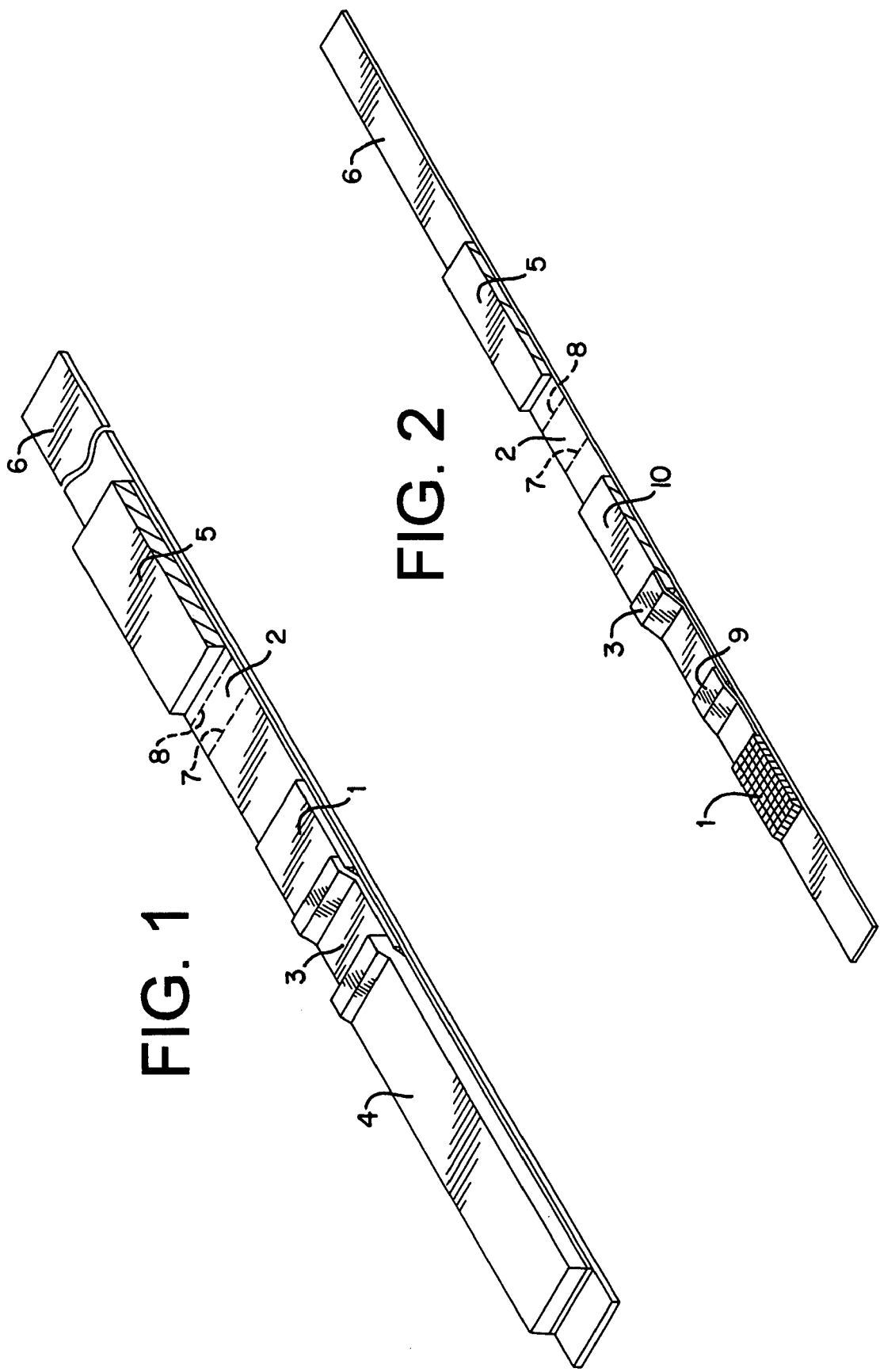

ANALYTE DETERMINATION USING A GENERAL PURPOSE STRUCTURE OF AN ANALYTICAL ELEMENT

CROSS-REFERENCE TO RELATED APPLICATIONS

This application is a continuation of U.S. patent application Ser. No. 09/215,979, filed Dec. 18, 1998, now U.S. Pat. No. 6,703,196,which claims the benefit of German Application Serial No. 197 57 980.9 filed Dec. 24, 1997 and German Application Serial No. 198 16 550.1 filed Apr. 15, 1998.

BACKGROUND OF THE INVENTION

1. Field of the Invention

The invention concerns an analytical element for the determination of an analyte containing in or on material which enables liquid transport between zones, a sample application zone and a detection zone located downstream thereof, wherein the detection zone contains a partner 1 of a specific binding pair 1 immobilized in such a manner that it is able to bind with partner 2 of the specific binding pair 1 which is not the analyte when this contacts it as well as a method for the determination of an analyte by means of specific binding pairs. The invention additionally concerns a kit for the determination of an analyte containing an analytical element.

2. Description of Related Art

Analytical elements are known from the prior art in which the reagents required to determine an analyte are present in or on carrier materials. Examples are: U.S. Pat. No. 4,861,711, U.S. Pat. No. 5,591,645 and EP-A-0 291 194. A common feature of the analytical elements described in these documents is that they are especially suitable for carrying out immunological detection methods. They comprise a sample application zone and a detection zone which is located downstream thereof. A liquid sample migrates through various zones between the sample application zone and detection zone as a result of capillary forces within a porous carrier material and thereby takes up the reagents that are necessary for detecting the analyte and reacts them with the analyte in the sample.

A binding partner is immobilized in the detection zone which is able to specifically bind the analyte to be determined. In the case of different analytes this requires that different binding partners for the analyte have to be immobilized on a solid phase.

It is also known from FIG. 1 of U.S. Pat. No. 4,861,711 in conjunction with the description, for example in column 5, line 57 to column 6 line 48 that a partner 1 of a specific binding pair 1 can be immobilized in the detection zone which does not bind the analyte but can be used universally because it binds an epitope as partner 2 of the specific binding pair 1 which is present on a substance which specifically binds the analyte. Hence the mobile complex of analyte and this binding substance is immobilized in the detection zone during the course of the detection reaction and is separated from non-complexed mobile reaction components.

A labelled substance that is specific for the analyte plays a very important role because only its binding to the analyte and the later immobilization of the complex formed composed of analyte and labelled substance directed against the analyte in the detection zone as well as the removal of the mobile non-reacted reaction components from the detection zone is able to indicate the presence of analyte in the liquid sample. The labelled substances known from the prior art are specific for the analyte i.e. in the case of sandwich assays they are labelled substances such as antibodies or antigens which react specifically with the analyte to be determined (antigen or antibody). However, this requires that depending on the analyte, different labelled specific binding partners for the analyte have to be prepared.

Numerous substances are known from the prior art for labelling. Whereas in the past radioactive labels with all their disadvantages were used, these labels were later replaced mainly by enzyme labels. Nowadays particulate labels, especially gold or latex particles, are mainly used in analytical elements as described in the previously described documents of the prior art. The preparation of a conjugate composed of a label and a substance binding specifically to the analyte is complicated and has to be optimized for each individual analyte-specific binding partner if it is intended to determine different analytes. In addition in analytical elements the material on which this conjugate is present and transported must be optimally adapted to the requirements from case to case. In this connection above all stability problems have often to be solved.

Therefore the object of the present invention was to provide a general purpose structure of an analytical element which can always be used independent of the analyte to be determined provided this analyte or a substance derived from the analyte and representing this analyte can be detected by specific pair binding.

SUMMARY OF THE INVENTION

The invention in particular concerns an analytical element for the determination of an analyte containing in or on material which enables liquid transport between zones, a sample application zone and a detection zone located downstream thereof, wherein the detection zone contains a partner 1 of a specific binding pair 1 immobilized in such a manner that it is able to bind to partner 2 of the specific binding pair 1 which is not the analyte when it contacts it, characterized in that a labelled partner 1 of a specific binding pair 2 is present upstream of the detection zone impregnated on a material such that it can be detached by liquid and is able to bind to partner 2 of the specific binding pair 2 which is not the analyte when this contacts it, in which partner 2 of the specific binding pair 1 and partner 2 of the specific binding pair 2 are specifically bound to the analyte to be determined or by reaction involving the analyte to be determined are parts of a substance derived from and representing the analyte.

The invention also concerns a kit for the determination of an analyte containing an analytical element as characterized above as well as additionally containing at least one partner from the group of partner 2 of the specific binding pair 1 and partner 2 of the specific binding pair 2.

Finally the invention also concerns a method for the determination of an analyte by means of specific binding pairs characterized in that a substance derived from and representing the analyte which comprises partner 2 of a specific binding pair 1 and partner 2 of a specific binding pair 2 is contacted in an analytical element according to the invention for the determination of an analyte with a labelled partner of the specific binding pair 2, is moved by liquid transport in the analytical element towards the detection zone which is upstream of the sample application zone, is bound in the detection zone to partner 1 of the specific binding pair 1 and is determined on the basis of the label of partner 1 of the specific binding pair 2.

BRIEF DESCRIPTION OF THE FIGURES

FIG. 1 is a perspective view of a general purpose analytical element according to the invention.

FIG. 2 is a perspective view of an integrated analytical element according to the invention.

DETAILED DESCRIPTION

An essential feature of the analytical element according to the invention is that liquid can move within the analytical element towards the detection zone. Such a liquid flow is for example possible by gravitational force in an appropriately prepared hollow body. Devices which enable liquid transport by centrifugal force as a type of gravitational force are known for example from EP-B 0 052 769. However, analytical elements according to the invention preferably contain absorbent materials which are able to move liquid by capillary force. The materials of the individual zones of the analytical element according to the invention can in this connection be the same or different. It will often be the case that different zones are composed of different materials if these are to optimally fulfil their function.

Suitable potential absorbent capillary-active materials are basically all those which can be used to take up liquid in so-called dry tests as described for example in U.S. Pat. No. 4,861,711, U.S. Pat. No. 5,591,645 or EP-A-0 291 194. Porous materials such as membranes, for example nitrocellulose membranes have proven to be advantageous. However, it is also possible to use fibrous, absorbent matrix materials such as fleeces, fabrics or knitted fabrics. Fleeces are particularly preferred. Fibrous matrix materials can contain, glass, cellulose, cellulose derivatives, polyester, polyamide and also viscose, artificial wool and polyvinyl alcohol. Fleeces made of cellulose-based fibres, polymer fibres based on polyester and/or polyamide and an organic binding agent which has OH and/or ester groups as known from EP-B-0 326 135 can for example be used according to the invention. Fleece materials containing meltable copolyester fibres in addition to glass fibres, polyester fibres, polyamide fibres, cellulose fibres or cellulose derivative fibres as described in the European patent application 0 571 941 can also be used in the analytical element according to the invention. Papers such as tea bag paper are also suitable.

In order to improve the handling of the analytical element according to the invention, the absorbent capillary-active material or different absorbent capillary-active materials can be arranged on a stiff carrier material which is itself impermeable to liquid, does not negatively influence the liquid flow in the matrix material and is inert with regard to the reactions that occur on the analytical element. Polyester foil can be a preferred carrier material on which the matrix material enabling liquid transport is attached.

In the analytical element according to the invention the individual zones can be arranged on the carrier material on top of each other, next to one another or partially on top of and partially next to one another. An analytical element according to the invention is particularly preferred in which the sample application zone and detection zone are arranged next to one another on the carrier material. In this connection next to one another means that these zones are adjacent and in direct contact with one another or are arranged essentially in one plane separated by other zones.

The sample application zone is the region of the analytical element according to the invention on which the sample is applied in which it is intended to determine whether a particular analyte or a substance derived from and representing this analyte is present and optionally in which amount it is present.

The detection zone is the region of the analytical element according to the invention in which it is determined whether the examined analyte or the substance derived from and representing the analyte was present in the sample applied to the analytical element. This determination can be qualitative, semiquantitative or quantitative. In this connection semiquantitative means that a specific concentration value is not determined for the analyte or for the substance derived from and representing the analyte but rather a concentration range is determined in which the analyte concentration is located.

Partner 1 of a specific binding pair 1 is immobilized in the detection zone in such a way that it is able to bind to partner 2 of the specific binding pair 1 which is not the analyte when this contacts it. The immobilization can be achieved by chemical reaction i.e. by formation of a covalent bond. However, it can also be achieved by adsorptive forces which includes all possibilities except for the formation of covalent bonds. A nitrocellulose membrane is frequently used for the detection zone to which proteins and also nucleic acids bind tightly when impregnated but without covalent binding.

According to the invention a labelled partner 1 of a specific binding pair 2 must also be in the analytical element in addition to partner 1 of a specific binding pair 1. This partner must not be immobilized but must be present in an impregnated form that can be detached by liquid i.e. it must be possible to transport this labelled partner by liquid towards the detection zone. Advantageously it should be possible to completely i.e. quantitatively detach this labelled partner by as little liquid as possible from the matrix material on which it is impregnated. Fleeces have proven to be particularly suitable as a matrix material for this as described for example in EP-B-0 326 135.

Specific binding pairs are known from the prior art and include for example pairs such as hapten and antibody, antigen and antibody, lectin and sugar or saccharide, avidin or streptavidin and biotin as well as nucleic acid and nucleic acid, ligand and receptor. In this connection an antigen can be any molecule against which one can experimentally produce antibodies. An antigen can also be an antibody or a particular site of an antibody which is referred to as an epitope and is specifically recognized and bound by an antibody. Nucleic acids should be understood as all possible forms of nucleic acids which are able to bind via complementary bases. DNA, RNA and also nucleic acid analogues such as peptide nucleic acids (PNA see for example WO 92/20702) are specifically mentioned but are not a definitive list. Ligand and receptor quite generally refer to a specific binding interaction between two partners such as between a hormone and hormone receptor.

In a preferred embodiment of the analytical element according to the invention, partner 1 of a specific binding pair 1 is an antibody which recognizes an epitope on another antibody which is directed against the analyte. The epitope against which the antibody is directed then corresponds to partner 2 of the specific binding pair 1. However, avidin or streptavidin are especially preferably used as partner 1 of the specific binding pair 1 which can specifically bind to biotin. Biotin then forms partner 2 of the specific binding pair 1.

In a preferred embodiment of the analytical element according to the invention partner 1 of the specific binding pair 2 is an antibody to partner 2 of the specific binding pair 2. This partner 2 of the specific binding pair 2 is preferably a hapten according to the invention, advantageously a hapten which is not present in the sample to be examined. Digitoxigenin, digitoxin, digoxigenin or digoxin are particularly preferably used as the hapten.

Basically all labels which are known for immunoassays from the prior art are suitable as a label of the partner 1 of the specific binding pair 2. These are in particular radioactive labels or enzyme labels such as peroxidase, alkaline phosphatase or galactosidase or fluorophores. However, so-called direct labels are particularly preferably used i.e. labels whose colour can be recognized by the eye without further handling steps. Advantageous labels of this type are for example particles that are insoluble in water such as metal or latex particles and also pigments such as silicate, carbon black or selenium. Metal particles in particular are preferably used as a label according to the invention. Colloidal gold is particularly preferred as a label. The label can be covalently or adsorptively bound to partner 1 of the specific binding pair 2 in which adsorptive includes all possibilities except for covalent binding. In the case of coloured latex particles as a direct label, a covalent bond is preferably present. Adsorptive bonds are preferably used for colloidal metals as direct labels in particular for colloidal gold.

The preparation of antibody-gold conjugates is for example known from Roth, J. The colloidal gold marker system for light and electron microscopic cytochemistry, in Bullock, G. R. and Petrusz, P. eds, Techniques in Immunocytochemistry, vol.2, New York, Academic Press, 1983, p. 216–284.

The labelled partner 1 of the specific binding pair 2 can be located at different sites of the analytical element according to the invention. This depends for example on the intended reaction procedure, on the amount of available sample or depends on the analyte concentration if the analytical element is for the determination of liquid samples.

Thus the labelled partner 1 of the specific binding pair 2 can be located in the sample application zone, it can be arranged downstream of the sample application zone between the sample application zone and the detection zone or can also be located upstream of the sample application zone. A prerequisite of at least the latter case is that the analytical element according to the invention also has an elution agent application zone in addition to the sample application zone. Such an elution agent application zone is then either located upstream of the region where the labelled partner 1 of the specific binding pair 2 is located or this region where the labelled partner 1 of the specific binding pair 2 is present is identical with the elution agent application zone. Hence an elution agent application zone can be present upstream of the sample application zone or at the site of the sample application zone on the analytical element according to the invention. Such an elution agent application zone is then always provided independent of where the labelled partner 1 of the specific binding pair 2 is located when the sample to be examined is not liquid or does not represent sufficient liquid for the determination of the analyte i.e. for the transport of the analyte and the required reagents into the detection zone.

A structure as described above of an analytical element according to the invention is universally suitable for the determination of any analyte which can be detected by specific pair binding. For this a substance derived from and representing the analyte which comprises partner 2 of a specific binding pair 1 and partner 2 of a specific binding pair 2 is contacted with the labelled partner 1 of a specific binding pair 2 in an analytical element according to the invention, is moved by liquid transport in the analytical element towards the detection zone which is located upstream of the sample application zone, is bound in the detection zone to partner 1 of the specific binding pair 1 and is determined on the basis of the label of partner 1 of the specific binding pair 2. For this determination it is particularly advantageous when mobile reaction components that are not immobilized in the detection zone are removed from the detection zone by liquid. If in the case of a liquid sample, the sample liquid is not sufficient to remove the mobile, non-immobilized reaction component from the detection zone, additional liquid can be applied to the analytical element in which case this application can be on the sample application zone or on a specific elution agent application zone.

The substance representing the analyte can be produced in different ways. In the case of an antigen as the analyte, it is for example possible to react the analyte with two antibodies which bind to the analyte. In this case one of the two antibodies carries partner 2 of the specific binding pair 1 and the other antibody carries partner 2 of the specific binding pair 2. If the analyte for example contains several copies of a particular epitope it is possible that the two antibodies are identical. According to the invention it is not absolutely necessary that the mixture of analyte, antibody with partner 2 of the specific binding pair 1 and antibody with partner 2 of the specific binding pair 2 are not contacted with partner 1 of the specific binding pair 2 on the analytical element according to the invention until the sandwich complex between the two antibodies and analyte has been completely formed. Ultimately it is important that the detection zone contains a bound sandwich complex on partner 1 of the specific binding pair 1 at the time of determining the analytical result. This sandwich formation can already be completed when the mixture of analyte and the two sandwich-forming antibodies are applied to the analytical element according to the invention, it can, however, also still be carried out during liquid transport of the reagents between the sample application zone and detection zone. In the extreme case the completion of the sandwich reaction takes place in the detection zone. The term "substance derived from and representing the analyte" therefore also includes a mixture of components that produce such a substance provided these components result in the substance derived from and representing the analyte in the detection zone.

If an antibody is determined as an analyte, antigens or oligopeptides representing the antigen epitope can be used as the analyte instead of the two antibodies in analogy to the previously described reaction in which case part of the antigen molecule carries partner 2 of the specific binding pair 1 and the other part of the antigen molecule carries partner 2 of the specific binding pair 2. For the determination a double antigen sandwich complex of the antibody to be determined and in each case one antigen with partner 2 of the specific binding pair 1 and one antigen with partner 2 of the specific binding pair 2 is formed for which the previous description for antigen determination applies analogously.

The structure of the general purpose analytical element according to the invention is also extremely suitable for the determination of nucleic acids. For this the nucleic acid to be determined must often be amplified in order to have adequate amounts available for a detection. This can for example be carried out by means of the polymerase chain reaction (PCR) or ligase chain reaction (LCR) known to a person skilled in the art. In the case of an amplification by means of PCR in which, starting with an oligonucleotide that is used as a primer, nucleotides are linked to a nucleic acid that is complementary to the nucleic acid to be determined and linked to the primer, partner 2 of the specific binding pair 1 or partner 2 of the specific binding pair 2 can for example be incorporated into the copy of the nucleic acid bound to such a nucleotide or a primer. If the amplification product obtained in this manner is hybridized with nucleic acid which carries partner 2 of that binding pair which the complementary amplified nucleic acid does not have, a substance derived from and representing the analyte is available that is fixed to the immobilized partner 1 of the specific binding pair 1 in the detection zone on the analytical element according to the invention and has been made determinable by the labelled partner of the specific binding pair 2.

Furthermore it is possible to omit amplification if adequate amounts of nucleic acid are available or to carry out the amplification of the nucleic acid without partner 2 of the specific binding pairs 1 or 2. Subsequently the substance representing the analyte is produced by hybridizing two probes which in each case carry partner 2 of the specific binding pair 1 and partner 2 of the specific binding pair 2.

Particularly preferably a nucleotide carrying partner 2 of the specific binding pair 1 or partner 2 of the specific binding pair 2 mixed with unlabelled nucleotides is used to amplify a nucleic acid to be determined and the amplified nucleic acid carrying partner 2 of the specific binding pair 1 or partner 2 of the specific binding pair 2 is hybridized with a nucleic acid which carries partner 2 of that specific binding pair which was not present in the nucleotide mixture used for the amplification. Thus a nucleic acid double strand is obtained in which each strand carries different partners of specific binding pairs. Instead of a nucleotide carrying partner 2 of the specific binding pair 1 or partner 2 of the specific binding pair 2, it is also possible to use an oligonucleotide carrying just this partner as a primer together with unlabelled nucleotides. Biotin is particularly preferably used as partner 2 of the specific binding pair 1 and a hapten such as fluorescein, rhodamine, digoxin or quite preferably digoxigenin is used as partner 2 of the specific binding pair 2. When using primers, those have proven to be particularly advantageous which are biotinylated.

Since biotinylated nucleotides and primers are commercially available or kits are available which enable the preparation of such substances like nucleic acids or nucleic acid fragments carrying haptens such as fluorescein, rhodamine, digoxin or especially digoxigenin, a person skilled in the art can very easily obtain substances derived from and representing nucleic acids to be determined especially for research purposes and rapidly and simply detect them by means of the analytical element according to the invention.

It is of course also possible to provide a kit for the determination of analytes which not only contains the general purpose analytical element according to the invention but also partner 2 of the specific binding pair 1 or partner 2 of the specific binding pair 2 or both partners. These partners are for example conjugated to a nucleotide, oligonucleotide, a nucleic acid, an antibody, a hapten or an antigen or an epitope or to a lectin or to a receptor for a ligand. These substances have the previously elucidated meaning. Thus it is possible to provide an interested person with components or all the necessary additional reagents for the determination of a special analyte in addition to the general purpose analytical element. In this connection it is unimportant whether partner 2 of the specific binding pair 1 and partner 2 of the specific binding pair 2 are present in separate containers or together in one container. This applies particularly to such systems in which the analyte to be determined is detected by means of two antibodies or by means of antigens via a sandwich complex. If it is intended to assemble a kit for the determination of a nucleic acid, it is advantageous that nucleotides or primers carrying partner 2 of the specific binding pair 1 or partner 2 of the specific binding pair 2 are stored separately from a nucleic acid complementary to the nucleic acid to be determined which carries partner 2 of that specific binding pair which is different from the partner which is conjugated with the nucleotide or with the primer.

The described general purpose analytical element according to the invention is particularly advantageous for analyte determinations in research and development where the analyte can be very different. The analytical element according to the invention can be used particularly advantageously especially for the determination of nucleic acids. A wide variety of nucleotides and oligonucleotides which are conjugated with partner 2 of a specific binding pair 1 or partner 2 of a specific binding pair 2 are commercially available. The same also applies to nucleic acid probes carrying partner 2 of a specific binding pair 1 or partner 2 of a specific binding pair 2 which can be easily prepared with commercially available kits. In particular nucleic acid probes carrying biotin and/or digoxin or digoxigenin can be easily obtained in this manner.

The general purpose structure of the analytical element according to the invention is also advantageous because the labelled binding partner usually represents a critical component in immunoassays with labelled binding partners of the analyte. Previously it was common practice to prepare a correspondingly labelled binding partner depending on the analyte for which optimal conditions for reaction and storage have then to be created on the analytical element. In the past this required a large amount of work. The analytical element according to the invention now provides an element which can be used universally. The specific reagents can be prepared at short notice and at lower costs as liquid reagents. Optimization work is not necessary especially with regard to the shelf-life of such reagents on analytical elements.

Furthermore it is, however, also possible, if this is desired, to not only use the analytical element according to the invention as a universal analytical element together with the specific reagents as liquid reagents but also to produce an analytical element starting with the analytical element according to the invention which contains the required totality of all reagents for the specific detection of an analyte. Thus for an antigen test by means of sandwich complex formation the required antibodies can be present integrated on an analytical element according to the invention provided one is conjugated with partner 2 of a specific binding pair 1 and the other is conjugated with partner 2 of a specific binding pair 2. The same also applies to an analytical element according to the invention which is intended for the detection of an antibody by means of sandwich complex formation. In this case a part of the antigen required is present integrated on the analytical element conjugated with partner 2 of a specific binding pair 1 and the other part of the antigen is present conjugated with partner 2 of a specific binding pair 2. Such conjugates can be arranged in a common zone or in zones of the analytical element according to the invention which are adjacent to one another, on top of one another or next to one another. In this case the two conjugates can be accommodated in the sample application zone or one of the conjugates can be accommodated in the sample application zone and the other in the zone between the sample application zone and detection zone or both conjugates can be accommodated separately or together in a zone between the sample application zone and detection zone. If an elution agent zone is arranged upstream of the sample application zone, it is also possible, in addition to the previously described possibilities, that the antigens or antibodies carrying partner 2 of the specific binding pairs 1 and 2 are arranged separately or together between the elution agent zone and sample application zone. Such analytical elements containing all necessary reagents for the determination of an analyte have the advantages of the simple and universal structure according to the invention and are extremely simple to handle for the user since only one sample has to be applied but otherwise no further handling steps are necessary before the result is read in the detection zone.

An analytical element according to the invention can also be used to determine at least one of several analytes. For example when samples are nowadays examined for a HIV infection it is necessary to determine whether one or several antibody types i.e. antibodies against HIV 1, against HIV 2 or against HIV 1 subtype 0 are present. The presence of antibodies against one type is sufficient to assess a sample as positive. Against which type the antibodies found are exactly directed is only of secondary importance at least in screening methods. An analytical element according to the invention which is suitable for such a determination contains in each case a pair of antigen conjugates against each antibody for which a sample is to be examined. Each pair contains antigen conjugated with partner 2 of the specific binding pair 1 and antigen conjugated with partner 2 of the specific binding pair 2 in which case the antigen binds specifically to a particular antibody type. The antigen conjugates can in each case be present separately. It is, however, also possible to mix all antigen conjugates and to accommodate them together in one zone. The previous general explanations for conjugates of antigens or antibodies with partners 2 of specific binding pairs 1 and 2 apply to the location of such conjugates in an analytical element according to the invention.

An analogous analytical element for the determination of influenza can detect the presence of influenza viruses A and/or influenza viruses B. Conjugates of antibodies against influenza A viruses with partners 2 of the specific binding pairs 1 and 2 as well as conjugates of antibodies against influenza viruses B with partners 2 of the specific binding pairs 1 and 2 are used for this. If at least one of the two virus types is present the analytical element according to the invention shows a positive result in the detection zone.

Furthermore it is also possible that an analytical element according to the invention contains additional functional zones. For example it has proven to be advantageous for the examination of whole blood to provide a zone in the analytical element according to the invention in which plasma or serum is separated as a clear liquid from whole blood and blood cells are retained. Only the clear liquid is then transported into the detection zone. Glass fibre fleeces as described in EP-A-0 045 476 are for example suitable for the separation of plasma or serum from whole blood. Such a medium suitable for separating plasma or serum from whole blood can for example be located in the sample application zone or between the sample application zone and detection zone.

The general purpose structure of the analytical element according to the invention provides a basis which greatly simplifies the development of analytical elements which carry all reagents for the detection of one or several analytes compared to the previously required development work and hence development times can be shortened.

Two particularly preferred analytical elements according to the invention are shown in FIGS. 1 and 2.

FIG. 1 shows a general purpose analytical element according to the invention which contains a carrier foil (6), an elution agent application zone (4), a zone containing a labelled partner 1 of the specific binding pair 2 (3), a sample application zone (1), a detection zone (2) with a colourless detection line (7) containing immobilized partner 1 of the specific binding pair 1 and a colourless control line (8) containing an antibody against partner 1 of the specific binding pair 2, as well as a liquid collection zone (5). The zones are arranged next to one another essentially in one plane on the carrier foil (6) in which "next to one another" in this case includes a slight overlap in each case of the previous zone in the liquid transport direction with the following zone so that liquid transfer from one zone into the other is ensured.

The analytical element according to the invention which is shown in FIG. 2 is a completely integrated analytical element i.e. it has all reagents required to carry out an analyte determination. It is also suitable for the examination of whole blood. Arranged next to one another on a carrier foil (6) are a sample application zone (1),
a zone containing the partners 2 of the specific binding pairs 1 and 2 (9),
a zone containing labelled partner 1 of the specific binding pair 2 (3),
a plasma or serum separation zone (10),
a detection zone (2) with a colourless detection line (7) containing the immobilized partner 1 of the specific binding pair 1 and a colourless control line (8) which contains an antibody against partner 1 of the specific binding pair 2
as well as a liquid collection zone (5).

The invention is elucidated further by the following examples.

EXAMPLES

Example 1

Determination of Nucleic Acid
a) Analytical Element

A test strip according to FIG. 1 was prepared. The following were attached next to one another and slightly overlapping to a 5 mm wide and 10 cm long carrier foil (6) made of polyester (MELINEX®, 350 µm thick from Imperial Chemistry Industries, Great Britain) using hot-melt adhesive (DYNAPOL®S 1358 from the Hüls AG, Germany)

a 1.5 mm thick and 1.5 cm long fleece composed of 100 parts glass fibres (diameter 0.49 to 0.58 µm, length 1000 µm) and 5 parts polyvinylalcohol fibres (KURALON®VPB 105-2 from Kuraray) with an area weight of 180/m² as the liquid collection zone (5), a 1.5 cm long cellulose nitrate membrane (type CN 11301 from Sartorius, Germany) as the detection zone (2), an 8 mm long fleece containing 80 parts polyester fibres, 20 parts artificial wool and 20 parts polyvinyl alcohol with a thickness of 0.32 mm and an area weight of 80 g/m², the manufacture of which is described in example 1 of the European Patent document 0 326 135 as the sample application zone (1), an 8 mm long fleece composed of 80 parts polyester fibres, 20 parts artificial wool and 20 parts polyvinyl alcohol fibres with a thickness of 0.32 mm and an area weight of 80 g/m², the manufacture of which is described in example 1 of the European Patent document 0 326 135 containing gold conjugate as the zone with the labelled partner of the specific binding pair 2 (3) and a 30 mm long fleece (type Binzer TI 05 from Binzer, Germany) as the elution agent application zone (4).

Concerning the Detection None (2):

An aqueous streptavidin solution (7 mg/ml) was applied by line dosing to the previously described cellulose nitrate membrane. For this purpose the dosage was selected such that a line with a width of ca. 0.5 mm was formed. The line (7) serves to detect the analyte to be determined. The membrane is subsequently dried in air.

An aqueous solution of a polyclonal antibody of rabbit IgG against mouse IgG (source: DAKO Diagnostica GmbH, Hamburg, Germany) (0.5 mg/ml) was applied by line dosing at a distance of about 4 mm from the streptavidin line. Also in this case the dosage was selected so that a line with a width of ca. 0.5 mm was formed. This line (8) serves as a control of the test strip function. The membrane was subsequently dried in air.

Concerning the Gold Conjugate Fleece (3):

Gold sol with an average particle diameter of ca. 40 nm was prepared according to the method of Frens (Frens, G., Preparation of gold dispersions of varying particle size: controlled nucleation for the regulation of the particle size in monodisperse gold suspensions in Nature: Physical Science 241 (1973), 20–22) by reduction of a 0.01 percent by weight tetrachloroauric solution with trisodium citrate while boiling.

The antibody gold conjugate was prepared in accordance with the method of Roth, J. The colloidal gold marker system for light and electron microscopic cytochemistry in Bullock, G. R. and Petrusz, P., eds., Techniques in Immunocytochemistry, vol. 2, New York, Academic Press, 1983, 216–284.

After cooling the previously described gold sol solution to room temperature, the pH value of the gold sol was adjusted with 0.2 M $K_2CO_3$ so that it was about 0.5 to 1.0 pH units above the isoelectric point of the antibody. The optical density (OD) of the gold sol (absorbance at 525 nm and 1 cm light path) was typically 1.0. A dialysed solution of a monoclonal IgG antibody against digoxygenin (MAB <digoxygenin> IgG) (source Boehringer Mannheim GmbH, Germany) was added to the gold sol. The amount of antibody solution was selected such that its concentration in the gold sol solution was typically 2 µg/ml. After 30 minutes stirring at room temperature the gold conjugate was saturated by adding a highly concentrated bovine serum albumin solution (final concentration in the conjugate solution: 1 mg/ml).

The gold conjugate was concentrated by ultrafiltration against a 20 mM Tris buffer pH 8.0 to an optical density of typically 20. The conjugate solution was subsequently admixed to a final concentration of 100 µM BRIJ® and 0.05% by weight $NaN_3$.

The gold conjugate prepared in this manner (optical density, OD=20) was adjusted with an impregnation buffer at a volume ratio 1:1 to an optical density, OD=10. The impregnation buffer contained the following components:

1% by weight sucrose
200 mM HEPES
100 mM NaCl
140 mM urea
6 mM N-acetylcysteine
2 mM EDTA
0.1% by weight TWEEN®20.

The polyester-artificial-wool-polyvinyl alcohol mixed fleece was pulled at a constant speed firstly through a tank containing the impregnation solution, subsequently squeezed between two stainless steel rollers spaced at a distance of 250 µm and subsequently dried by means of a circulating air drier. Under the described conditions the impregnation uptake of the fleece is typically about 270 ml/m².

b) Determination of an Amplification Product of *Chlamydia trachomatis*

A fragment of the cryptic plasmid (7.5 Kb) of *Chlamydia trachomatis* with 143 base pairs was amplified. For this the primers of the *Chlamydia trachomatis* primer and capture probe set (Boehringer Mannheim, Germany) were used (primer 1:20-mer, position 274–295; primer 2:24-mer, position 393–416 rev).

The labelling was carried out with DIG-11-dUTP (DIG stands for digoxigenin) and a 5' biotinylated capture probe (Boehringer Mannheim GmbH, Germany).

The PCR master mixture contained 2.5 U Taq polymerase, 10 µl 10-fold PCR buffer including 25 mmolar magnesium chloride, 0.2µ molar of both primers, 0.1 mmolar of each deoxynucleotide and 0.02 mmolar DIG-11-dUTP. This results in a labelling stoichiometry of 1:5 DIG-11-dUTP to deoxynucleotides. The master mix was filled up to 100 µl by adding by pipette 10 µl of a solution which contained ca. 100 copies/µl of the cryptic plasmid fragment and distilled water. The master mix was melted for 10 minutes at 94° C. and ran through 35 cycles in which each time it was kept for 40 seconds at 94° C., 30 seconds at 52° C. and 45 seconds at 72° C. The PCR product was checked in a 2.5% agarose gel which was stained with ethidium bromide.

For the hybridization 1 µl of a 5' biotin-labelled capture probe (position 354–374) was added at a concentration of 30 µmolar to 50 µl of the amplification product. The labelled capture probe was thus present at a concentration of 0.6 µmolar. The sample was subsequently melted for 5 minutes at 95° C. and subsequently hybridized for 15 minutes at 37° C.

In order to determine the nucleic acid on the previously described test strip according to FIG. 1, 5 µl of the hybridization product was applied to the sample application zone (1). Afterwards the elution agent application zone (4) of the test strip was immersed for 5 seconds in a chromatography buffer whereby care must be taken that zone (3) containing the gold conjugate is not immersed in the liquid. The chromatography buffer had the following composition: 0.9% by weight sodium chloride, 50 mM potassium phosphate, 0.09% by weight sodium azide, 2% by weight bovine plasma albumin and 0.25% by weight TWEEN® 20.

After 10 minutes the chromatography buffer had migrated from the elution agent application zone (4) into the liquid collection zone (5). 2 red lines were clearly visible in the detection zone (2), whereby the red detection line (containing streptavidin) indicates a positive result and the red control line (containing PAB <MOUSE Fcγ>) indicates the correct function of the analytical element.

Example 2

Detection of Influenza A/B Viruses
  a) Analytical Element

A test strip according to FIG. 1 was prepared. The components of the analytical element were identical to those described in example 1 apart from the control line in the detection zone (2). In this case a solution of a polyclonal antibody of rabbit IgG against mouse IgG was used for the control line (source: DAKO Diagnostica GmbH, Hamburg, Germany).
  b) Influenza-Specific Immunoreagents Antibodies for the detection of the nucleoprotein of influenza A and influenza B viruses were obtained from Fitzgerald Industries Int., Concord, Mass., USA.

In order to prepare a biotin-labelled monoclonal antibody of mouse IgG against the nucleoprotein of influenza A, a succinimide ester derivative of biotin was added in a 6-fold molar excess to a solution of 20 mg/ml antibody in 0.1 M potassium phosphate pH 8.5. The mixture was incubated for 90 minutes at 25° C. while stirring. The reaction was stopped by supplementing the solution with lysine to a final concentration of 10 mM. The excess biotinylation reagent was removed by dialysis and the solution was frozen.

A biotinylated monoclonal antibody against the nucleoprotein of influenza B was prepared in a similar manner.

For the preparation of a digoxigenylated monoclonal antibody against the nucleoprotein of influenza A, a succinimide ester derivative of digoxigenin dissolved in dimethylsulfoxide (DMSO) was added in a 4-fold molar excess to a solution of 10 mg/ml of the monoclonal antibody in 0.1 M potassium phosphate in such a manner that the final concentration of DMSO in the solution was 5 vol %. The mixture was incubated for 60 minutes at 25° C. while stirring. The reaction was stopped by adding a 1 molar aqueous lysine solution so that the final concentration of lysine was 10 mM. The excess digoxigenylation reagent was removed by dialysis against a 20 mM potassium phosphate buffer pH 8.0 and the solution was frozen until use.

A digoxigenylated monoclonal antibody against the nucleoprotein of influenza B was prepared similarly to the previously described digoxigenylation of the monoclonal antibody against the nucleoprotein of influenza A.

The influenza A and influenza B antibodies used are type-specific i.e. the influenza A antibody only recognizes the nucleoprotein of influenza A viruses whereas the monoclonal influenza B antibody only recognizes the nucleoprotein from influenza B viruses. However, the antibodies are not subtype-specific i.e. the monoclonal antibody against influenza A recognizes all influenza A subtypes.
  c) Determination of Influenza A and/or Influenza B Viruses Diluted virus culture supernatants were used as a sample material to demonstrate the sensitivity of the analytical element according to the invention. The viruses were cultured on MDCK cells, a permanent dog kidney cell strain. The incubation was carried out in the usual culture medium for about 7 days at 33° C. The subtype H3N2 (strain Beijing 32/92) was cultured as a representative of influenza A and the strain B/harbin 7/94 was cultured as a representative of influenza B. The culture supernatants were diluted with culture medium in two-fold steps.

65 µl culture supernatant from each different dilution, 15 µl lysis buffer (6% Zwittergent®3–10 in physiological saline containing bovine serum albumin) and in each case 5 µl of a solution of biotinylated monoclonal antibody against influenza A and digoxigenylated monoclonal antibody against influenza A were pipetted into an Eppendorf vessel for the detection of influenza A or 5 µl of a solution of biotinylated monoclonal antibody against influenza B and 5 µl digoxigenylated monoclonal antibody against influenza B were pipetted into an Eppendorf vessel (the concentration of the antibody conjugate stock solutions was in each case 20 µg/ml). The lysed sample was briefly homogenized by shaking and subsequently 80 µl was pipetted onto the gold conjugate fleece (3) of the test strip according to FIG. 1. Subsequently the elution agent application zone (4) of the test strips was immersed for ca. 5 seconds in the chromatography buffer (0.9% by weight sodium chloride, 50 mM potassium phosphate, 0.09% by weight sodium azide, 2% by weight bovine plasma albumin and 0.25% by weight Tween® 20). The test result in the detection zone (2) was read after 10 minutes.

A red detection line indicating a positive result was observed in the case of the influenza A culture supernatant up to a culture dilution of 1:64. In the case of the influenza B culture supernatant the dilutions were recognized as positive up to the 1:128 step. In all cases the red colour of the control line indicated the correct function of the test strip.

Example 3

Detection of HIV Antibodies
  a) Analytical Element

A test strip according to FIG. 2 was prepared. The following were attached next to one another and slightly overlapping to a 4 mm wide and 10 cm long carrier foil (6) made of polyester (MELINEX®, 350 µm thick from Imperial Chemistry Industries, Great Britain) using hot-melt adhesive (DYNAPOL®S 1358 from the Hüls AG, Germany)

a 0.9 mm thick and 1.4 cm long fleece composed of 100 parts glass fibres (diameter 0.49 to 0.58 µm, length 1000 µm) and 5 parts polyvinylalcohol fibres (KURALON®VPB 105-2 from Kuraray) with an area weight of 100 g/m² as the liquid collection zone (5), a 1.5 cm long cellulose nitrate membrane (type CN 11301 from Sartorius, Germany) as the detection zone (2), a 1.2 cm long fleece made of 100 parts glass fibres (diameter 0.49 to 0.58 µm, length 100 µm) and 5 parts polyvinyl alcohol fibres (KURALON®VPB 105-2 from Kuraray) with an area weight of 100 g/m² which is impregnated with BRIJ® (1% by weight) as a plasma or serum separation zone (10), a 12 mm long fleece containing 80 parts polyester fibres, 20 parts artificial wool and 20 parts polyvinyl alcohol fibres with a thickness of 0.32 mm and an area weight of 80 g/m², the manufacture of which is described in example 1 of the European Patent document 0 326 135, containing gold conjugate as a zone containing the labelled partner of the specific binding pairs 2 (3), a 12 mm long fleece composed of 80 parts polyester fibres, 20 parts artificial wool and 20 parts polyvinyl alcohol fibres with a thickness of 0.32 mm and an area weight of 80 g/m², the manufacture of which is described in example 1 of the European Patent document 0 326 135 containing digoxigenylated and biotinylated HIV antigens as a zone containing the partners 2 of the specific binding pairs 1 and 2 (9) and an 8 mm long polyester fabric (PE 280 HC from Seidengaze Thal, Switzerland) impregnated with a wetting agent as the sample application zone (1).

Concerning the Detection Zone (2):

An aqueous streptavidin solution (4 mg/ml) was applied by line dosing to the previously described cellulose nitrate membrane. For this purpose the dosage was selected such that a line with a width of ca. 0.4 mm was formed. This line serves to detect HIV antibodies. The membrane was subsequently dried in air.

An aqueous solution of a polyclonal antibody of rabbit IgG against mouse IgG (source: DAKO Diagnostica GmbH, Hamburg, Germany) (0.5 mg/ml) was applied by line dosing at a distance of about 4 mm from the streptavidin line. Also in this case the dosage was selected so that a line with a width of ca. 0.4 mm was formed. This line (8) serves as a control of the test strip function. The membrane was subsequently dried in air.

Concerning the Gold Conjugate Fleece (3):

Gold sol with an average particle diameter of ca. 40 nm was prepared as described in example 1a.

The antibody-gold conjugate was also prepared as described in example 1a.

The gold conjugate prepared in this manner (optical density, OD=20) was adjusted with an impregnation buffer to an optical density, OD=3 (absorbance at 525 nm and 1 cm light path). The impregnation buffer contained the following components:
100 mM HEPES, pH 7.5
50 mM NaCl
0.5% by weight sucrose
70 mM urea
3 mM N-acetylcysteine
1 mM EDTA and
0.1% by weight Tween®20.

The polyester-artificial-wool-polyvinyl alcohol mixed fleece was pulled at a constant speed firstly through a tank containing the impregnation solution, subsequently squeezed between two stainless steel rollers spaced at a distance of 250 μm and subsequently dried by means of a circulating air drier. Under the described conditions the impregnation uptake of the fleece is typically about 270 ml/m$^2$.

Concerning Fleece (9) Containing Digoxigenylated and Biotinylated HIV Antigens:

The preparation of digoxigenylated peptides and biotinylated peptides from the gp 41 region of HIV I are described in example 1 of U.S. Pat. No. 5,804,371. The respective peptides were in each case used pair-wise as digoxigenin and biotin derivatives. Their mixing concentrations in the impregnation solution were between $0.7 \cdot 10^{-7}$ mol/l and $3 \cdot 10^{-7}$ mol/l. In addition the impregnation solution contained
100 mM MES buffer, pH 6.0
50 mM NaCl
2% by weight sucrose
1% by weight bovine serum albumin
3 mM N-acetylcysteine
0.06% by weight TWEEN® 20
1 mM EDTA The polyester-artificial-wool-polyvinylalcohol mixed fleece was impregnated in this impregnation solution and subsequently dried by means of a circulating air drier. The impregnation uptake is typically about 270 ml/m$^2$.

b) Determination of a HIV Infection.

About 60 μl sample volume (plasma or serum) was applied to the sample application zone (1) of the previously described test strip according to FIG. 2. After 15 minutes waiting time, the detection zone (2) was evaluated visually. A red-violet line at the position of the control line (8) indicates non-reacted sample (no HIV infection detectable). Two red-violet lines, one at the position of the control line (8) and one at the position of the detection line (7) indicate a reactive sample (HIV infection detectable).

What is claimed is:

1. A method for determining an analyte in a sample using an analytical element, the method comprising:
   providing a mixture by contacting the sample with a binding partner 2 of a specific binding pair 1 (partner 2 of pair 1), and a binding partner 2 of a specific binding pair 2 (partner 2 of pair 2), wherein partner 2 of pair 1 and partner 2 of pair 2 are not the analyte and wherein partner 2 of pair 1 and partner 2 of pair 2 bind the analyte when the analyte is present in the sample, wherein the mixture is provided before the mixture is added to the element;
   adding the mixture to a sample application zone of the analytical element, wherein the element comprises a material enabling liquid transport between the sample application zone and a detection zone located downstream thereof, wherein the partner 2 of pair 1 and the partner 2 of pair 2 are not immobilized on the material, wherein the detection zone comprises a binding partner 1 of specific binding pair 1 (partner 1 of pair 1) immobilized in such a manner that it is able to bind to the partner 2 of pair 1, and wherein a labeled partner 1 of specific binding pair 2 (partner 1 of pair 2) is present upstream of the detection zone and impregnated on the material such that it can be detached by liquid and is able to bind to the partner 2 of pair 2,
   forming, when the analyte is present in the sample, a complex comprising the partner 1 of pair 1, the partner 2 of pair 1, the analyte, the partner 1 of pair 2 and the partner 2 of pair 2, and
   detecting the presence or absence of the label in the detection zone, thereby determining the analyte in the sample.

2. The method of claim 1 wherein the specific binding pair 1 and the specific binding pair 2 independently comprise a pair of specific binding partners selected from the group consisting of a hapten and an antibody, an antigen and an antibody, a lectin and a sugar/saccharide, a ligand and a receptor, avidin/streptavidin and biotin, a nucleic acid and a nucleic acid.

3. The method of claim 1 wherein the partner 1 of pair 2 is an antibody against the partner 2 of pair 2.

4. The method of claim 3 wherein the partner 1 of pair 2 is an antibody against digoxigenin or digoxin.

5. The method of claim 1 wherein the partner 1 of pair 2 is labeled with an enzyme or direct label.

6. The method of claim 5 wherein metal or latex particles are used as the direct label.

7. The method of claim 1 wherein the partner 1 of pair 2 is located in the sample application zone.

8. The method of claim 5 wherein the partner 1 of pair 2 is located in the sample application zone.

9. The method of claim 1 wherein an antibody for specific binding with an antigen or hapten is conjugated with the partner 2 of pair 1 and the antibody is conjugated with the partner 2 of pair 2.

10. The method of claim 1 wherein an antigen, hapten or oligopeptide is conjugated with the partner 2 of pair 1 and the antigen, hapten or oligopeptide is conjugated with the partner 2 of pair 2, wherein the antigen, hapten or oligopeptide specifically binds to an antibody.

11. The method of claim 1 wherein the partner 2 of pair 1 and the partner 2 of pair 2 are in separate containers prior to providing the mixture, wherein the separate containers do not include the analytical element.

12. The method of claim 1 wherein the partner 2 of pair 1 and the partner 2 of pair 2 are stored together in one container prior to providing the mixture, wherein the container does not include the analytical element.

13. The method of claim 1 wherein the partner 2 of pair 1 is conjugated to a nucleotide, oligonucleotide, a nucleic acid, an antibody, a hapten or antigen or an epitope representing an antigen or a lectin or a receptor for a ligand.

14. The method of claim 13 wherein the partner 2 of pair 1 is biotin.

15. The method of claim 1 wherein the partner 2 of pair 2 is conjugated to a nucleotide, oligonucleotide, a nucleic acid, an antibody, a hapten or antigen or an epitope representing an antigen or a lectin or a receptor for a ligand.

16. The method of claim 15 wherein the partner 2 of pair 2 is a hapten.

17. The method of claim 16 wherein wherein the hapten is digoxigenin or digoxin.

18. A method for determining the presence of an analyte using an analytical element comprising a material enabling liquid transport between a sample application zone and a detection zone located downstream thereof, wherein the detection zone comprises a binding partner 1 of specific binding pair 1 (partner 1 of pair 1) immobilized in such a manner that it is able to bind to a binding partner 2 of specific binding pair 1 (partner 2 of pair 1), and wherein a labeled partner 1 of specific binding pair 2 (partner 1 of pair 2) is present upstream of the detection zone and impregnated on the material such that it can be detached by liquid and is able to bind to a specific binding partner 2 of specific binding pair 2 (partner 2 of pair 2); the method comprising:

adding to the element at the sample application zone a substance derived from and representing the analyte wherein the substance comprises partner 2 of pair 1 and partner 2 of pair 2 bound to the analyte, wherein partner 2 of pair 1 and partner 2 of pair 2 are not the analyte and are not present on the element prior to the addition of the substance to the element and wherein the substance is formed before it is added to the element, and moving the substance by liquid transport in the analytical element towards the detection zone wherein the partner 2 of pair 2 binds the partner 1 of pair 2; and binding the substance to partner 1 of pair 1 in the detection zone; and detecting the labelled partner 1 of pair 2 bound in the detection zone, thereby determining the presence of the analyte.

19. The method of claim 18 wherein the substance derived from and representing the analyte is formed by adding to the analyte an antibody wherein part of the antibody comprises partner 2 of pair 1 and the other part of the antibody comprises partner 2 of pair 2.

20. The method of claim 18 wherein the substance derived from and representing the analyte is formed by adding to the analyte an antigen, hapten or oligopeptide wherein a part of the antigen, hapten or oligopeptide comprises partner 2 of pair 1 and the other part of the antigen, hapten or oligopeptide comprises partner 2 of pair 2.

21. The method of claim 18 wherein the analyte is a nucleic acid which is amplified, whereby partner 2 of pair 1 or partner 2 of pair 2 is bound to a nucleotide or to an oligonucleotide that is incorporated into the amplification product of said nucleic acid, and the amplification product is hybridized with a complementary nucleic acid having partner 2 of pair 1 or partner 2 of pair 2 bound thereto, provided that when the amplification product has partner 2 of pair 1 bound thereto, the complementary nucleic acid has partner 2 of pair 2 bound thereto and when the amplification product has partner 2 of pair 2 bound thereto, the complementary nucleic acid has partner 2 of pair 1 bound thereto.

22. The method of claim 18 wherein the analyte is a nucleic acid and said substance comprises the nucleic acid hybridized with two nucleic acid probes one of which contains partner 2 or pair 1 and the other contains partner 2 of pair 2.

* * * * *